United States Patent [19]

Mo et al.

[11] Patent Number: 5,583,280
[45] Date of Patent: Dec. 10, 1996

[54] AIR BUBBLE SENSOR WITH SIMPLIFIED MOUNTING OF PIEZO ELEMENTS

[75] Inventors: Frank S. C. Mo, Redwood City; Michael E. Kelly, Mountain View; Peter A. Holst, Castro Valley, all of Calif.

[73] Assignee: Abbott Laboratories, Abbott Park, Ill.

[21] Appl. No.: 378,835

[22] Filed: Jan. 26, 1995

[51] Int. Cl.$^6$ .................................................. G01N 30/02
[52] U.S. Cl. ................ 73/19.03; 73/866.5; 128/DIG. 12
[58] Field of Search ............................... 73/19.03, 866.5; 128/DIG. 12, DIG. 13

[56] References Cited

U.S. PATENT DOCUMENTS

| | | | |
|---|---|---|---|
| 4,114,144 | 9/1978 | Hyman | 340/632 |
| 4,418,565 | 12/1983 | St. John | 73/19 |
| 4,651,555 | 3/1987 | Dam | 73/19 |
| 4,673,927 | 6/1987 | Cianciavicchia et al. | 340/621 |
| 4,758,228 | 7/1988 | Williams | 604/123 |
| 4,764,166 | 8/1988 | Spani | 604/65 |
| 4,821,558 | 4/1989 | Pastrone et al. | 73/19 |
| 4,950,244 | 8/1990 | Fellingham et al. | 604/118 |
| 5,064,412 | 11/1991 | Henke | 604/65 |
| 5,102,392 | 4/1992 | Sakai et al. | 604/122 |
| 5,177,993 | 1/1993 | Beckman et al. | 73/19.03 |
| 5,269,188 | 12/1993 | Esin et al. | 73/610 |
| 5,394,732 | 3/1995 | Johnson et al. | 73/19.1 |

*Primary Examiner*—Hezron E. Williams
*Assistant Examiner*—Jay L. Politzer
*Attorney, Agent, or Firm*—Ronald M. Anderson

[57] ABSTRACT

A system and method for mounting a piezoelectric crystal and forming electrical connections to it in an air bubble sensor (10). Piezoelectric crystals (26, 54) are mounted against inner surfaces of two opposed cavities (16, 44) using a conductive epoxy. The conductive epoxy both adhesively secures the crystals in place and provides conductive paths to adjacent conductive pins (28, 30, 46, and 48). To mount one of the piezoelectric crystals, a drop of the conductive epoxy is placed on an inner planar surface of the cavity and the crystal is pushed into the conductive epoxy, forcing the conductive epoxy to flow from under the crystal and into contact with one of the conductive pins. The inner end of another conductive pin is bent over the crystal and a drop of the conductive epoxy is then placed on the outwardly facing surface of the piezoelectric crystal, electrically and mechanically coupling the end of the conductive pin that was bent over, to the outwardly facing surface of the crystal. One of the piezoelectric crystals is electrically excited at its resonant frequency, producing ultrasonic sound waves used to detect gaseous bubbles in a liquid flowing through an intravenous (IV) line disposed in a gap(42) formed between two upright supports (14, 40) in which the piezoelectric crystals are mounted. Bubbles in the line attenuate the ultrasonic signal received by the other piezoelectric crystal, reducing an output electrical signal that it produces in response.

25 Claims, 3 Drawing Sheets

AIR BUBBLE SENSOR WITH SIMPLIFIED MOUNTING OF PIEZO ELEMENTS

FIELD OF THE INVENTION

This invention generally relates to sensors used to detect gas bubbles within a liquid, and more specifically, to a gas bubble sensor in which a transducer is adhesively mounted within a support cavity and to a system and method for mounting the transducer.

BACKGROUND OF THE INVENTION

One of the more common applications for a sensor capable of detecting gas bubbles in a liquid arises in the field of medicine, in connection with pumps used to infuse liquids into a patient. Most intravenous (IV) pumps employ an air bubble sensor to monitor the IV lines carrying liquid from the pump to a patient, to detect air bubbles. The air bubble sensors respond to bubbles larger than a predetermined maximum size, but also detect smaller air bubbles. Even relatively small air bubbles can create a problem if their density or total volume is sufficient to produce a potentially life threatening air embolism should the small bubbles combine within the patient's cardiovascular system to form a large air bubble.

An air bubble sensor suitable to detect bubbles in an IV line typically includes two piezoelectric crystals that are mounted in a housing on each side of a slot. The IV line carrying liquid to the patient is inserted into the slot so that it contacts the inner surfaces of the housing on each side of the slot. One of the piezoelectric crystals is electrically excited at its resonant frequency to produce ultrasonic sound waves that are directed transversely through the IV line toward the other piezoelectric crystal. The other crystal resonates at approximately the same ultrasonic frequency as the transmitting crystal, and in response to the ultrasonic sound waves that it receives, produces a corresponding electrical output signal. Since liquid is a much better conductor of ultrasonic sound than is air, any gaseous bubbles entrained in the liquid that flows through the IV line between the transmitting and receiving piezoelectric crystals will attenuate the ultrasonic sound waves reaching the receiving crystal in a manner indicative of gas bubble size and density. Changes in the magnitude of the ultrasonic sound waves received produce a corresponding change in the electrical signal output from the receiving crystal. A monitoring circuit is coupled to the receiving crystal and responds to the electrical output signal. This monitoring circuit typically stops the pump and produces an audible and/or visual alarm if either too many small gas bubbles or a gas bubble that is larger than a predetermined maximum is detected.

A prior art air bubble sensor used by the assignee of the present invention employs a housing comprising two plastic halves—one half supporting the piezoelectric crystal that generates the ultrasonic sound waves and the other half supporting the piezoelectric crystal that receives the ultrasonic sound waves after they have passed through the sensor cavity or slot. When assembled, the two halves of the housing define a slot of an appropriate width to receive an IV line, with the transmitting crystal mounted within one half of the housing on one side of the slot and the receiving crystal mounted opposite, within the other half of the housing. Care must be taken to ensure that the transmitting piezoelectric crystal is properly aligned with the receiving crystal when the two halves of the sensor are assembled. Small errors in the alignment can adversely affect the performance of the sensor.

In this prior art sensor, the steps involved in mounting each piezo element within its respective half of the housing are relatively involved, time consuming, and labor intensive. Specifically, each piezoelectric crystal used in the sensor is first mounted on a separate alumina substrate, which serves as a carrier. Before the crystals are mounted on their respective carriers, a pattern of electrically conductive paths and pads of palladium-silver alloy are applied to the alumina substrate, e.g., by silk screening. A piezoelectric crystal is then affixed to the alumina substrate using a conductive epoxy that electrically connects the downwardly facing surface of the crystal to one of the conductive paths on the alumina substrate. One end of a thin wire (actually two thin wires in parallel are preferably used to improve reliability) is then ultrasonically welded to a conductive pad applied to the alumina substrate; the other end of the wire is mechanically bonded to the outwardly facing surface of the piezoelectric crystal, with a drop of conductive epoxy added to reinforce the bond. The alumina substrate with the piezoelectric crystal mounted on it is then installed in a cavity within one of the two plastic housing halves, and conductive epoxy is used to connect the conductive paths on the alumina substrate to copper pins that extend externally of the housing. A non-conductive epoxy is used as a potting agent to cover the alumina substrate and copper pins, making an airtight seal over the assembly within the cavity. After each substrate mounted upon its carrier is thus installed within a cavity formed within one of the housing halves, the two plastic sections of the housing are assembled to form the air bubble sensor.

Clearly, it would be preferable to employ a system and method for mounting a piezoelectric crystal that is simpler than the prior art technique described above. It would be desirable to mold a single integral housing to support both the transmitting piezoelectric crystal and the receiving piezoelectric crystal. However, it is essential that any simpler mounting system not degrade the reliability of the air bubble sensor or reduce its sensitivity. An intermittent electrical connection between one of the piezoelectric crystals and the electrical signal path in the sensor or a loosened mount of the crystal could have potentially life threatening consequences if the air bubble sensor should fail to detect air bubbles. Any simplified system for mounting a piezoelectric crystal in an air bubble sensor must therefore ensure that the crystal remains firmly seated within its support and must ensure that a good electrical connection is maintained between the crystal and the external circuitry.

SUMMARY OF THE INVENTION

In accordance with the present invention, a transducer mounting system for a sensor usable to detect gaseous bubbles within a liquid is defined. The mounting system includes an integral housing for the transducer, having a cavity formed within it in which the transducer is mounted. A pair of conductive pins are provided. Each conductive pin has an internal end and an external end. The internal end of each conductive pin extends into the cavity, and the external end of each conductive pin extends beyond the supporting housing and is adapted to connect to an electrical circuit. These conductive pins are disposed adjacent different surfaces of the transducer.

An electrically conductive adhesive is disposed in two separate areas within the cavity. A first portion of the electrically conductive adhesive secures the transducer within the cavity and provides an electrically conductive path between one of the conductive pins and one surface of the transducer. Similarly, a second portion of the electrically conductive adhesive provides an electrically conductive path between a different surface of the transducer and the other conductive pin. The electrically conductive adhesive is employed to mount the transducer within the cavity and to convey an electrical signal between the transducer and the internal ends of the conductive pins.

The internal end of one of the conductive pins is preferably displaced to overlie one surface of the transducer. One of the two areas in which the electrically conductive adhesive is disposed is adjacent the internal end of the conductive pin that overlies the transducer. The electrically conductive adhesive is preferably applied as a drop on the outwardly facing surface of the transducer to which the internal end of this conductive pin is electrically and mechanically secured.

In the preferred embodiment, one of the conductive pins is generally aligned with a surface of the transducer that faces inwardly into the cavity, and the other conductive pin (which locks the transducer within the cavity) is not.

The surfaces of the transducer are generally planar, as is an inner surface of the cavity. The first portion of the electrically conductive adhesive comprises a film that adheres one of the planar surfaces of the transducer to the inner surface of the cavity. The film of electrically conductive adhesive extends beyond one edge of the transducer and contacts one of the conductive pins. Preferably, the electrically conductive adhesive comprises an epoxy. In the preferred embodiment, the transducer is a piezoelectric crystal that can function as either a transmitter or a receiver of an ultrasonic signal. To facilitate this application of the invention, the housing is formed of a material having the ability to conduct the ultrasonic signal.

Another aspect of the present invention is directed to a method for mounting a transducer. This method includes steps that are consistent with the functions performed by the elements of the system used for mounting a transducer that is discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
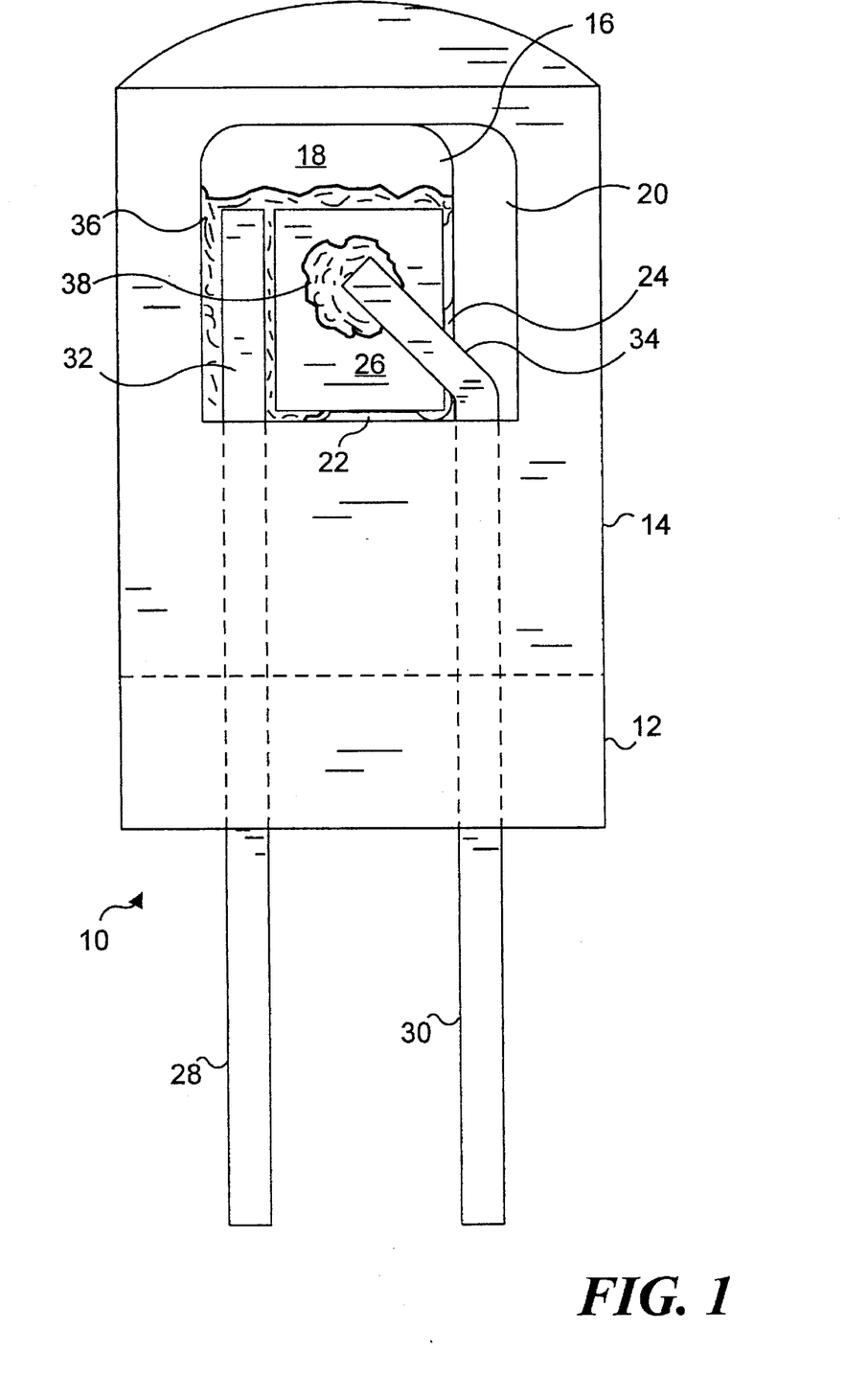
FIG. 1 is an elevational side view of an air bubble sensor (before sealing caps are installed) in which a piezoelectric crystal is mounted in accord with the present invention.
Figure 2:
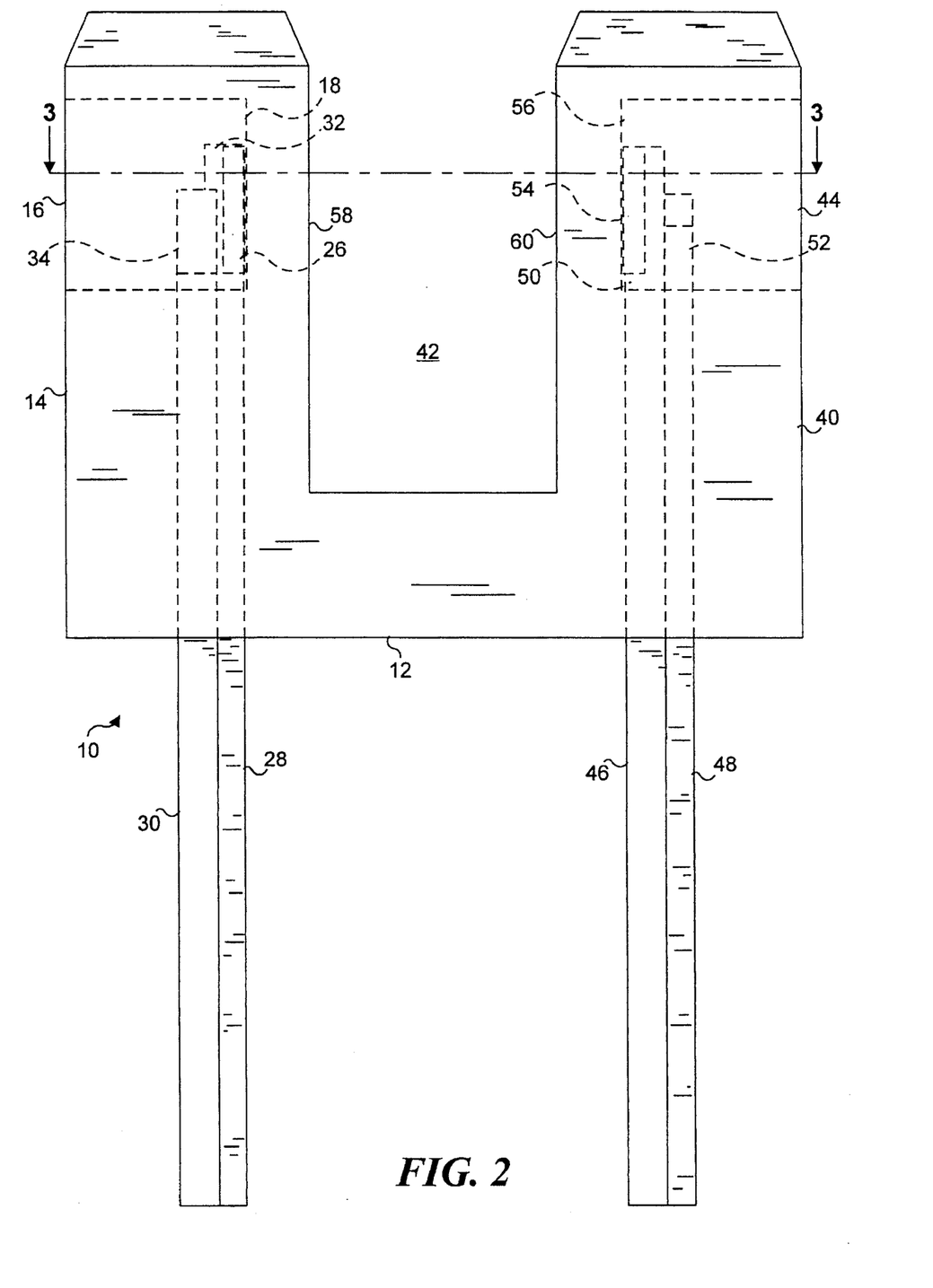
FIG. 2 is an elevational front view of the air bubble sensor of FIG. 1.
Figure 3:
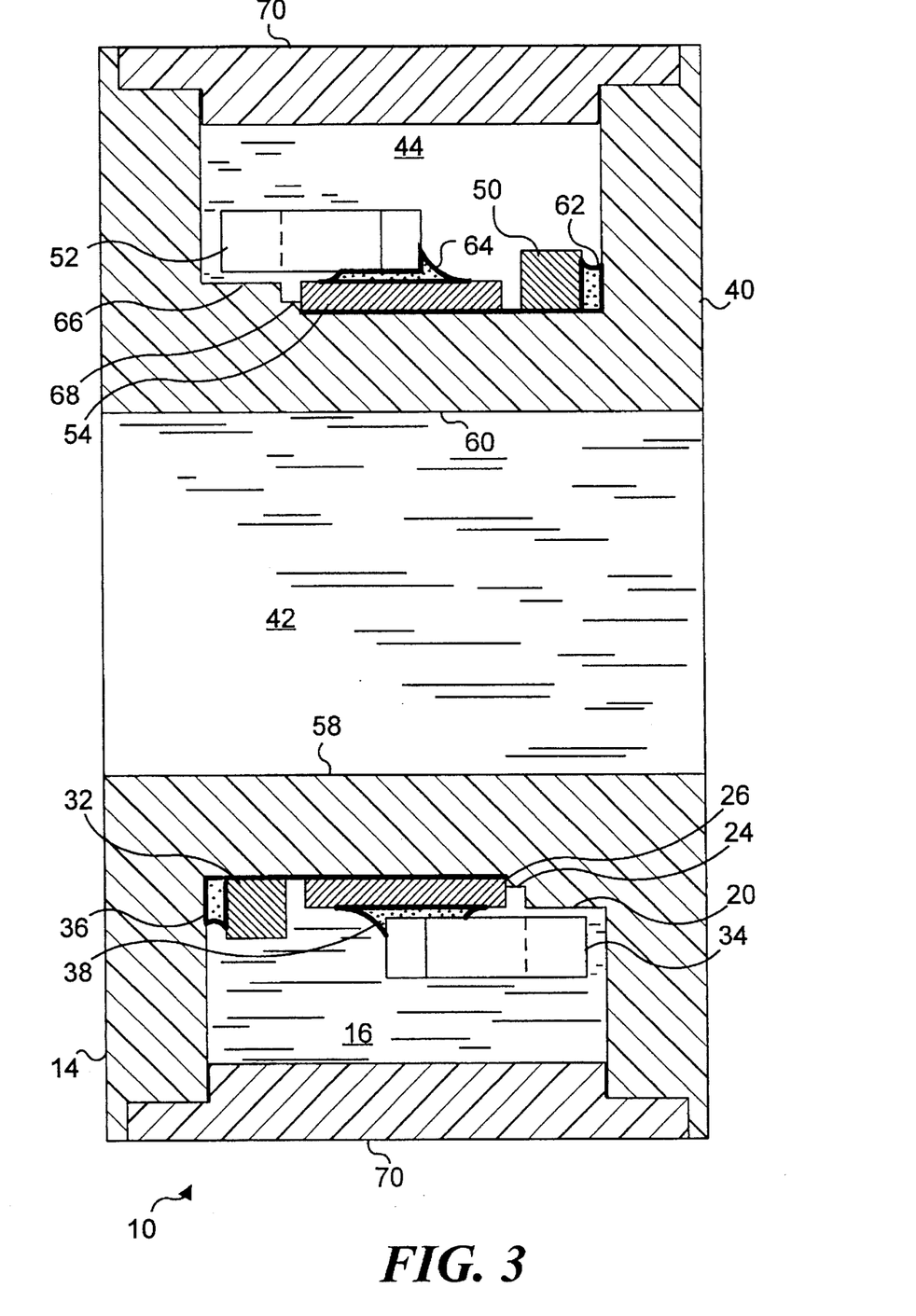
FIG. 3 is a cross-sectional view of the air bubble sensor, taken along section lines 3—3 in FIG. 2.

A preferred embodiment of an air bubble sensor 10 embodying the present invention is shown in FIGS. 1 through 3. It should be noted that the term "air bubble sensor" as used in this description and in the claims is intended to include a sensor that detects any gas bubbles in a liquid and is not limited to the detection of air bubbles, although air bubbles are most commonly the type of gaseous bubbles detected with this preferred embodiment. Turning first to FIG. 1, the side elevational view of the bubble sensor illustrates many of the features that enable it to be fabricated more efficiently and at substantially less cost than the prior art air bubble sensor described above in the Background of the Invention.

In the view shown in FIG. 1, it will be noted that air bubble sensor 10 includes a base 12 from which an upright support 14 extends at one side. In FIG. 2, a second upright support 40 is shown extending from base 12. The entire housing for air bubble sensor 10, i.e., base 12 and upright supports 14 and 40, is integrally injection molded, eliminating the need to join two separate halves together, which is a requirement of the prior art air bubble sensor described above.

Referring back to FIG. 1, upright support 14 includes a cavity 16 generally centered within its upper portion. A piezoelectric crystal 26 is mounted on an inner planar surface 18 of cavity 16. A generally planar shelf 20 is offset above, but in alignment with inner planar surface 18, running inside the cavity along the right edge. Inside along the lower edge of cavity 16 is disposed a guide 22. Similarly, along the lower right edge of shelf 20, within cavity 16, is disposed a guide 24. Guides 22 and 24 together assist in aligning piezoelectric crystal 26 when it is seated within cavity 16 during fabrication of air bubble sensor 10.

Shelf 20 provides a surface that is raised above inner planar surface 18 of the cavity, at approximately the same depth in the cavity as the outer surface of piezoelectric crystal 26. Shelf 20 thus defines the disposition of a conductive pin 30 within cavity 16, offsetting conductive pin 30 relative to a conductive pin 28.

In the preferred embodiment, the housing of air bubble sensor 10 is injection molded with appropriately sized holes formed in the injection molding process or afterward. Four conductive pins 28 and 30, and 46 and 48 are then press fit through the holes so that they extend into the cavities. Alternatively, it may be possible to mold the pins in place when the housing of the air bubble sensor is injection molded.

As shown in FIG. 1, conductive pins 28 and 30 extend downwardly, externally from base 12. These pins pass through base 12, and through upright support 14 into cavity 16. Each of the conductive pins have a generally square cross-sectional shape. As noted above, conductive pin 28 enters cavity 16 at a different depth than conductive pin 30. The inwardly facing surface of conductive pin 28 is generally aligned with inner planar surface 18 of cavity 16. Similarly, the inwardly facing surface of conductive pin 30 is generally aligned with the surface of shelf 20. An exposed inner end 32 of conductive pin 28 extends adjacent to and in alignment with the left side of piezoelectric crystal 26. Before piezoelectric crystal 26 is mounted within cavity 16, an exposed inner end 34 of conductive pin 30 extends into cavity 16, in alignment with the surface and left edge of shelf 20. However, once piezoelectric crystal 26 is mounted within cavity 16, exposed inner end 34 of the conductive pin is displaced or bent over, so that it overlies piezoelectric crystal 26, as shown in FIG. 1.

Before proceeding with the description of air bubble sensor 10, it will be helpful to describe the steps employed for mounting piezoelectric crystal 26 within cavity 16. Prior to inserting piezoelectric crystal 26 into cavity 16, a medium-sized drop of a conductive epoxy 36 is applied to inner surface 18 of cavity 16. Piezoelectric crystal 26 is positioned within cavity 16, so that its lower edge rests against guide 22, and its right edge against guide 24. The piezoelectric crystal is then forced against the drop of conductive epoxy 36, causing the conductive epoxy to spread out, forming a film between inner surface 18 and the inwardly facing surface of the crystal. Excess conductive epoxy 36 flows out around the periphery of the piezoelectric crystal into contact with one or more surfaces of exposed inner end 32 of conductive pin 28. Both the upper and downwardly facing surfaces of piezoelectric crystal 26 have a conductive layer (gold, silver, or other metallic material-not shown) applied thereon. Thus, the conductive layer on the downwardly facing surface of piezoelectric crystal 26 is electrically coupled through conductive epoxy 36 with conductive pin 28. When the conductive epoxy cures, it both adherently fastens the crystal within the cavity and forms a conductive path between conductive pin 28 and the downwardly facing surface of the crystal. In the preferred embodiment, ABLEBOND™ epoxy, type 967-1 is used.

After piezoelectric crystal 26 is thus adhesively mounted within cavity 16, exposed inner end 34 of conductive pin 30 is bent over so that it overlies the exposed surface of the piezoelectric crystal. Next, a small drop of conductive epoxy 38 is placed on the outwardly facing surface of the piezoelectric crystal and the bent over portion of exposed end 34 of conductive pin 30. Conductive epoxy 38 adhesively fastens piezoelectric crystal 26 to exposed end 34 of conductive pin 30 and forms a conductive path between the outwardly facing surface of piezoelectric crystal 26 and conductive pin 30. By bending over exposed end 34 of conductive pin 30 so that it overlies piezoelectric crystal 26, the crystal is mechanically locked into place within cavity 16. Both the adhesive properties of the conductive epoxy and the mechanical positioning of the exposed portion of conductive pin 30 securely mount the piezoelectric crystal in place within the cavity. Separate conductive paths are also formed between the opposite inwardly and outwardly facing surfaces of the piezoelectric crystal and conductive pins 28 and 30, respectively, by the two portions of the conductive epoxy.

Referring now to FIGS. 2 and 3, details of the rest of air bubble sensor 10 are shown. Opposite upright support 14, on the other side of base 12, is disposed upright support 40. Upright supports 14 and 40 have facing surfaces 58 and 60, respectively, between which is defined a gap 42. Within the upper portion of upright support 40 is disposed a cavity 44, generally open to the side of the air bubble sensor opposite to that in which cavity 16 is formed. In cavity 44, on an inner planar surface 56, is mounted a piezoelectric crystal 54. Cavity 44 includes a guide 68 along one side and a guide (not separately shown) along the lower edge of the cavity for aligning piezoelectric crystal 54 within the cavity so that it is disposed directly opposite piezoelectric crystal 26. A shelf 66 is also disposed along one side of cavity 44 providing a surface within the cavity approximately aligned with the outer facing surface of piezoelectric crystal 54.

Conductive pins 46 and 48 extend downwardly from base 12, as noted above, and through base 12 and upright support 40 into cavity 44. An exposed inner end 50 of conductive pin 46 extends generally along one side of and in alignment with piezoelectric crystal 54. Similarly, an exposed inner end 52 of conductive pin 48 is bent over to overlie the outwardly facing surface of piezoelectric crystal 54.

Piezoelectric crystal 54 is mounted and fixed within cavity 44 in substantially the same manner as piezoelectric crystal 26. A conductive epoxy 62 coats the inner surface of cavity 44, adhesively affixing the crystal in place and electrically connecting the inwardly facing surface of piezoelectric crystal 54 to exposed inner end 50 of conductive pin 46. After piezoelectric crystal 54 is thus affixed to the inner surface of cavity 44, exposed inner end 52 of conductive pin 48 is displaced or bent over so that it overlies the piezoelectric crystal and a drop of a conductive epoxy 64 is placed on the outwardly facing surface of the crystal. Conductive epoxy 64 adherently connects inner end 52 to the outwardly facing surface of piezoelectric crystal 54, providing an electrically conductive path between the exposed end of conductive pin 48 and the outwardly facing surface of the piezoelectric crystal. Finally, as shown in FIG. 3, caps 70 are adhesively bonded within the open side of each cavity 16 and 44, covering the open cavities and providing an airtight seal for the piezoelectric crystals mounted therein.

The air bubble sensor is normally connected to an air-in-line monitoring circuitry through conductive pins 28, 30, 46, and 48, using a suitable termination such as a printed circuit board (not shown). During use of air bubble sensor 10 on an IV pump, for example, an IV line (not shown) made of an elastomeric material is positioned within gap 42. This IV line has an outer diameter slightly greater than the distance between facing surfaces 58 and 60 of upright supports 14 and 40. The circumferential outer surface of the fluid line is forced into contact with facing surfaces 58 and 60 along two lines respectively adjacent to piezoelectric crystals 26 and 54. An ultrasonic sound wave is generated by one of the two piezoelectric crystals when it is excited by an electrical signal developed by the air-in-line circuit. Although either crystal can be used, in this example, the ultrasonic sound is produced by piezoelectric crystal 26. The applied electric signal is an alternating current (AC) signal that sweeps through a range of frequencies including the resonant frequency of the piezoelectric crystal. In response to the applied electric signal, piezoelectric crystal 26 produces a corresponding ultrasonic sound wave at its resonant frequency. This ultrasonic signal passes through the wall of cavity 16, through the IV tubing, and propagates transversely through liquid flowing through the tube. At the opposite side of gap 42, the ultrasonic sound wave propagates through facing surface 60 of upright support 40 and into cavity 44. The ultrasonic sound wave excites piezoelectric crystal 54 at its resonant frequency, causing the crystal to produce a corresponding AC electrical output signal having a magnitude generally indicative of the magnitude of the received ultrasonic sound wave. Any air (gas) bubbles within the liquid flowing through the IV tube within gap 42 tends to attenuate the ultrasonic sound wave received by piezoelectric crystal 54, reducing the magnitude of the electrical output signal that it produces. Accordingly, air bubble sensor 10 produces an output signal indicative of the size of the air bubbles within liquid flowing through the IV tube that is seated within gap 42.

By forming air bubble sensor 10 using an integrally formed injection molded housing in which cavities 16 and 44 are formed with substantially parallel inner surfaces, alignment of piezoelectric crystals 26 and 54 is ensured. The piezoelectric crystals are mounted directly to the inner surfaces of their respective cavities by the conductive adhesive film, thereby facilitating transmission of the ultrasonic sound wave through the thin wall of the upright supports in which the crystals are mounted.

It will be evident to those of ordinary, skill in the art that a somewhat different configuration for air bubble sensor 10 can be used to sense air bubbles in other shapes of liquid carrying devices. For example, it may be necessary to sense gas bubbles within a liquid in a cavity. The configuration of the sensor in which a piezoelectric crystal is mounted may readily be modified to accommodate such differing requirements. However, a piezoelectric crystal used in such differing configuration air bubble sensors can still be mounted in accord with the present invention. Accordingly, it is not intended that the present invention as disclosed in the exemplary configuration of air bubble sensor 10 should in any way be considered limiting on the scope of the claims. The present invention provides an efficient technique for both providing conductive paths to conductive pins and mounting a piezoelectric crystal (or other type of transducer) in almost any housing.

Therefore, although the present invention has been described in connection with one preferred form of practicing it, those of ordinary skill in the art will understand that many modifications can be made thereto within the scope of the claims that follow. Accordingly, it is not intended that the scope of the invention in any way be limited by the above description, but that it be determined entirely by reference to the claims that follow.

The invention in which an exclusive right is claimed is defined by the following:

1. An air bubble sensor for detecting bubbles in a fluid line, comprising:
    (a) a housing having a base portion and two opposed supports extending generally upright from the base portion in alignment with each other to form a U-shaped slot, said slot having a bottom defined by the base portion and sides defined by inner surfaces of the two opposed supports;
    (b) two cavities, each cavity being formed in one of the opposed supports, vertically displaced from the bottom of the base portion and generally disposed oppositely and in alignment with the other cavity;
    (c) four conductive pins, each conductive pin passing through the base portion and into the opposed supports, portions of two of the conductive pins extending into one of the cavities, and portions of the other two conductive pins extending into the other cavity; and
    (d) two piezo elements, one piezo element being disposed in one of the cavities and the other piezo element being disposed in the other cavity, each of said piezo elements having a first surface and a second surface that are separately respectively coupled to the two conductive pins, which extend into the cavity in which the piezo element is disposed, the first surface of the piezo element being coupled to one of the conductive pins and the second surface being coupled to the other conductive pin using a conductive adhesive, said conductive adhesive both supporting the piezo element in the cavity and providing a path for an electrical signal between the conductive pins and the first and second surfaces of the piezo element, one of the piezo elements producing an ultrasonic sound when excited by a driving electrical signal, and the other of the piezo elements producing an output electrical signal indicative of a magnitude of the ultrasonic sound received from the other of the piezo elements following transmission of the ultrasonic sound transversely through the fluid line, any air bubbles within a liquid in the fluid line tending to attenuate the ultrasonic signal that is received, as indicated by the output electrical signal wherein the portion of one of the two conductive pins extending into each cavity is bent over, to position the one conductive pin adjacent one of the first and second surfaces of the piezo element and a portion of the conductive adhesive extends between the first surface of the piezo element and the conductive pin that is bent over.

2. The air bubble sensor of claim 1, wherein the piezo elements comprise generally planar slabs of piezoelectric crystal, and wherein one of the first and second surfaces of each piezo element is adhesively bonded to a generally planar inner surface of the cavity by a film of the conductive adhesive, which extends into contact with one of the conductive pins.

3. The air bubble sensor of claim 1, wherein the portions of the two conductive pins that extend into each cavity are spaced apart from the side of the slot adjacent the piezo element with the end of one conductive pin bent to be disposed behind its respective piezo element.

4. The air bubble sensor of claim 1, wherein one of the conductive pins extending in to each cavity is disposed adjacent one side edge of the piezo element and the other of the conductive pins extending into said cavity is disposed adjacent an opposite side edge of the piezo element, offset back from the nearest side of the slot than said one conductive pin.

5. The air bubble sensor of claim 1, wherein the two opposed supports and the base portion of the housing are integrally formed as a single piece.

6. An air bubble sensor for detecting bubbles in a fluid line, comprising:
    (a) an integrally molded housing having a base portion and two opposed supports extending generally upright from the base portion in parallel alignment with each other to form a U-shaped slot, said slot having a bottom defined by the base portion and sides defined by inner surfaces of the two opposed supports;
    (b) two cavities, each cavity being formed in one of the opposed supports vertically displaced from the bottom of the base portion and having an inner surface generally disposed oppositely in alignment with an inner surface of the other cavity;
    (c) four conductive pins, each conductive pin passing through the base portion and into the opposed supports, portions of two of the conductive pins extending into one of the cavities, and portions of the other two conductive pins extending into the other cavity; and
    (d) two piezo elements, each of said piezo elements having a front surface and a back surface, the front surface of one piezo element being mounted directly on the inner surface of said one of the cavities, and the front surface of the other piezo element being mounted directly on the inner surface of said other cavity, said front and back surfaces of each piezo element being separately respectively electrically coupled to the two conductive pins that extend into the cavity in which the piezo element is dispose, one of the piezo elements producing an ultrasonic sound that is conducted through a thin wall of the support in which said one piezo element is conducted through a thin wall of the support in which said one piezo element is disposed, to the inner surface of said support, when said one piezo element is excited by a driving electrical signal, and the other of the piezo elements producing an output electrical signal indicative of a magnitude of the ultrasonic sound receive from the other of the piezo elements following transmission of the ultrasonic sound transversely through the fluid line and through the inner surface and an adjacent thin wall of the support in which said other of the piezo elements is disposed, any air bubbles within a liquid in the fluid line tending to attenuate the ultrasonic signal that is receive, as indicated by the output electrical signal.

7. The air bubble sensor of claim 6, wherein each of the piezo elements are directly mounted on the inner surface of the cavity with a thin film of conductive adhesive that electrically couples one of the conductive pins to the front surface of said piezo element.

8. The air bubble sensor of claim , wherein one of the conductive pins extending into each cavity is electrically coupled to the back surface of the piezo element mounted in said cavity.

9. The air bubble sensor of claim 6, wherein one of the conductive pins extending into each cavity is bent over and overlies the back surface of the piezo element mounted in said cavity.

10. The air bubble sensor of claim 9, wherein the conductive pin that is bent over is electrically coupled to the back surface of the piezo element mounted in said cavity with a conductive adhesive.

11. In a sensor for detecting gaseous bubbles within a liquid, a transducer mounting system comprising:

(a) an integral supporting housing for the transducer, said housing having a cavity formed within it in which the transducer is mounted;

(b) a pair of conductive pins, each conductive pin having an internal end and an external end, the internal end of each conductive pin extending into the cavity, and the external end of each pin extending beyond the supporting housing and being adapted to connect to an electrical circuit, said conductive pins being disposed adjacent different surfaces of the transducer; and (c) an electrically conductive adhesive disposed in two separate areas within the cavity, a first portion of the electrically conductive adhesive securing the transducer within the cavity and providing an electrically conductive path between one of the conductive pins and one surface of the transducer, a second portion of the electrically conductive adhesive providing an electrically conductive path between a different surface of the transducer and the other conductive pin, said electrically conductive adhesive mounting the transducer within the cavity and conveying an electrical signal between the transducer and the internal ends of the conductive pins.

12. The transducer mounting system of claim 11, wherein the internal end of one of the conductive pins is displaced to overlie one surface of the transducer.

13. The transducer mounting system of claim 12, wherein one of the two areas in which the electrically conductive adhesive is disposed is adjacent the internal end of the conductive pin that is displaced, said electrically conductive adhesive being applied to the surface of the transducer to which said internal end of the conductive pin is electrically and mechanically secured.

14. The transducer mounting system of claim 11, wherein one of the conductive pins has a front surface which is generally aligned with a front surface of the transducer that faces inwardly into the cavity, and the other conductive pin does not.

15. The transducer mounting system of claim 11, wherein the surfaces of the transducer are generally planar, as is an inner surface of the cavity, and wherein the first portion of the electrically conductive adhesive comprises a film that adheres a front planar surface of the transducer to the inner surface of the cavity, said film of electrically conductive adhesive extending beyond one edge of the transducer and contacting one of the conductive pins.

16. The transducer mounting system of claim 11, wherein the electrically conductive adhesive comprises an epoxy.

17. The transducer mounting system of claim 11, wherein the transducer is piezoelectric crystal that is adapted to function as one of a transmitter and a receiver of an ultrasonic signal, said housing being formed of a material selected for its characteristic ability to conduct the ultrasonic signal.

18. A method for mounting a transducer, comprising the steps of:

(a) forming a cavity in a supporting housing, said cavity having an inner surface that is generally planar and being sized to accept the transducer;

(b) providing a pair of conductive pins, each of which include an internal end and an external end, the pair of conductive pins being passed through the supporting housing so that their internal ends are disposed spaced apart within the cavity, and their external ends extend outside of the supporting housing being thereby adapted to couple to an external electrical circuit, and bending the internal end of one of the pair of conductive pins;

(c) placing a first portion of an electrically conductive adhesive on the inner surface of the cavity and on the internal end of the bent conductive pin;

(d) inserting the transducer into the cavity positioned so that an inwardly facing surface of the transducer is adhesively secured to the inner surface of the cavity by the electrically conductive adhesive and so that the first portion of the electrically conductive adhesive extends between the inwardly facing surface of the transducer and the internal end of the bent conductive pin; and (e) placing a second portion of the electrically conductive adhesive on an outwardly facing surface of the transducer and in contact with the other of the conductive pins, said first and second portions of the electrically conductive adhesive respectively conducting an electrical signal between the one conductive pin and the inwardly facing surface of the transducer, and between the other conductive pin and the outwardly facing surface of the transducer.

19. The method of claim 18, wherein the electrically conductive adhesive comprises an epoxy.

20. The method of claim 18, wherein the transducer comprises a piezoelectric crystal, said supporting housing being formed of a material able to conduct ultrasonic sound waves.

21. The method of claim 20, wherein the supporting housing comprises a fixture encompassing a slot, further comprising the step of mounting another piezoelectric crystal within another cavity formed in the fixture, in accord with steps (a) through (e), so that the slot is disposed between the two piezoelectric crystals, thereby enabling one of the piezoelectric crystals to transmit ultrasonic sound waves through a medium disposed within the slot, for receipt by the other piezoelectric crystal, in order to detect any gaseous bubbles in the medium.

22. A method for mounting a transducer that has generally planar front and back surfaces, comprising the steps of:

(a) forming a cavity in a supporting housing, said cavity having an inner surface that is generally planar and sized to accept the transducer;

(b) providing a pair of conductive pins, each of which include an internal end and an external end, the pair of conductive pins being passed through the supporting housing so that their internal ends are disposed spaced apart within the cavity, and their external ends extend outside of the supporting housing being thereby adapted to couple to an external electrical circuit, and bending the internal end of one of the pair of conductive pins;

(c) mounting the front surface of the transducer directly on the inner surface of the cavity; and (d) electrically coupling the internal ends of the conductive pins separately to said front and back surfaces of the transducer, respectively by applying an electrically conductive adhesive between the inner surface of the cavity and the transducer so that the electrically conductive adhesive extends between the front surface of the transducer and the internal end of the bent conductive pin.

23. The method of claim 22, wherein the supporting housing includes spaced apart supports for the transducer and a transmitter, respectively, further comprising the steps of repeating steps (a) through (d) to mount the transmitter directly on an inner surface of another cavity formed within its support so that the transmitter and transducer are spaced apart, substantially in parallel alignment with each other, said transmitter being thereby mounted so that a signal produced by the transmitter will propagate through the inner surface of the other cavity, through any object disposed in an intervening space between the two supports, and through the support housing for the transducer to be received by the transducer.

24. A method for mounting a transducer, comprising the steps of:

(a) forming a cavity in a supporting housing, said cavity having an inner surface that is generally planar and being sized to accept the transducer;

(b) providing a pair of conductive pins, each of which include an internal end and an external end, the pair of conductive pins being passed through the supporting housing so that their internal ends are disposed spaced apart within the cavity, and their external ends extend outside of the supporting housing being thereby adapted to couple to an external electrical circuit, and bending the internal end of one of the pair of conductive pins;

(c) placing a first portion of an electrically conductive adhesive on the inner surface of the cavity and on the internal end of the bent conductive pin;

(d) inserting the transducer into the cavity positioned so that an outwardly facing surface of the transducer is adhesively secured to the inner surface of the cavity by the electrically conductive adhesive and so that the first portion of the electrically conductive adhesive extends between the outwardly facing surface of the transducer and the internal end of the bent conductive pin; and (e) placing a second portion of the electrically conductive adhesive on an inwardly facing surface of the transducer and in contact with the other of the conductive pins, said first and second portions of the electrically conductive adhesive respectively conducting an electrical signal between the one conductive pin and the inwardly facing surface of the transducer, and between the other conductive pin and the outwardly facing surface of the transducer.

25. A method for mounting a transducer that has generally planar front and back surfaces, comprising the steps of:

(a) forming a cavity in a supporting housing, said cavity having an inner surface that is generally planar and sized to accept the transducer;

(b) providing a pair of conductive pins, each of which include an internal end and an external end, the pair of conductive pins being passed through the supporting housing so that their internal ends are disposed spaced apart within the cavity, and their external ends extend outside of the supporting housing being thereby adapted to couple to an external electrical circuit, and bending the internal end of one of the pair of conductive pins;

(c) mounting the first surface of the transducer directly on the inner surface of the cavity; and (d) electrically coupling the internal ends of the conductive pins separately to said front and back surfaces of the transducer, respectively, by applying an electrically conductive adhesive between the inner surface of the cavity and the transducer so that the electrically conductive adhesive extends between the back surface of the transducer and the internal end of the bent conductive pin.

* * * * *

UNITED STATES PATENT AND TRADEMARK OFFICE
CERTIFICATE OF CORRECTION

PATENT NO. : 5,583,280
DATED : December 10, 1996
INVENTOR(S) : Frank S.C. Mo, et al It is certified that error appears in the above-indentified patent and that said Letters Patent is hereby corrected as shown below:

On the title page, item [57] Abstract, line 21, "gap(42)" should read -- gap (42) --.
Column 4, line 23, "fight" should read -- right --.
Column 8, line 51, "dispose" should read -- disposed --
Column 8, lines 54-55, delete the words "is conducted through a thin wall of the support in which said one piezo element"
Column 9, line 6, "claim ," should read -- claim 6, --

Signed and Sealed this

Twenty-ninth Day of April, 1997

Attest:

BRUCE LEHMAN

Attesting Officer

Commissioner of Patents and Trademarks